United States Patent [19]

Moore et al.

[11] Patent Number: 5,252,787
[45] Date of Patent: Oct. 12, 1993

[54] STETHOSCOPE

[76] Inventors: Jerome Moore; Gwendolyn Moore, both of 3233 Wesley Chapel Rd., Decatur, Ga. 30034; Sidney L. Harley, 5470 Memorial Dr., Suite B, Stone Mountain, Ga. 30083

[21] Appl. No.: 697,784

[22] Filed: May 9, 1991

[51] Int. Cl.$^5$ .............................................. A61B 7/02
[52] U.S. Cl. ................................... 181/131; 181/137
[58] Field of Search ............... 181/131, 137; 368/276, 368/294, 295

[56] References Cited

U.S. PATENT DOCUMENTS

| D. 285,964 | 9/1986 | Ziebol | D24/17 |
| 323,654 | 8/1885 | Fenner | 368/295 |
| 3,910,376 | 10/1975 | Azneer | 181/131 |
| 4,802,550 | 2/1989 | Poore | 181/131 |

Primary Examiner—Michael L. Gellner
Assistant Examiner—Eddie C. Lee
Attorney, Agent, or Firm—Michael V. Drew

[57] ABSTRACT

A stethoscope head is combined with a watch having a sweeping second hand. A watch support member 30 extends from the stethoscope housing 20. The watch 32 rests upon the watch support member 30. A watch housing 38 encases the watch 32 and is secured to the watch support member 30. The watch support member 30 may be made of sound-absorbing material. Sound-absorbing material may be interposed between the stethoscope housing 20 and watch support member 30. The watch support member 30 and watch housing 38 may have cooperating threads so that the watch housing 38 may be screwed onto the watch support member 38. The sweeping second hand 34 of the watch may be easily viewed while the stethoscope is used.

4 Claims, 1 Drawing Sheet

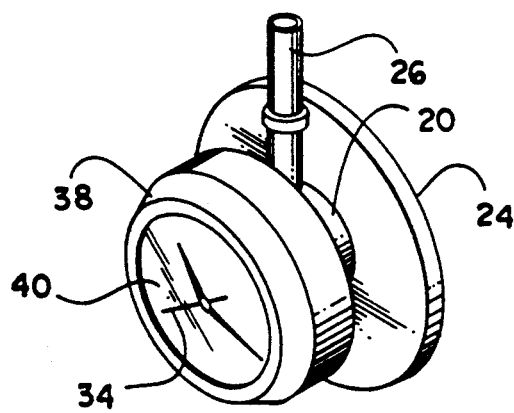
Fig_1
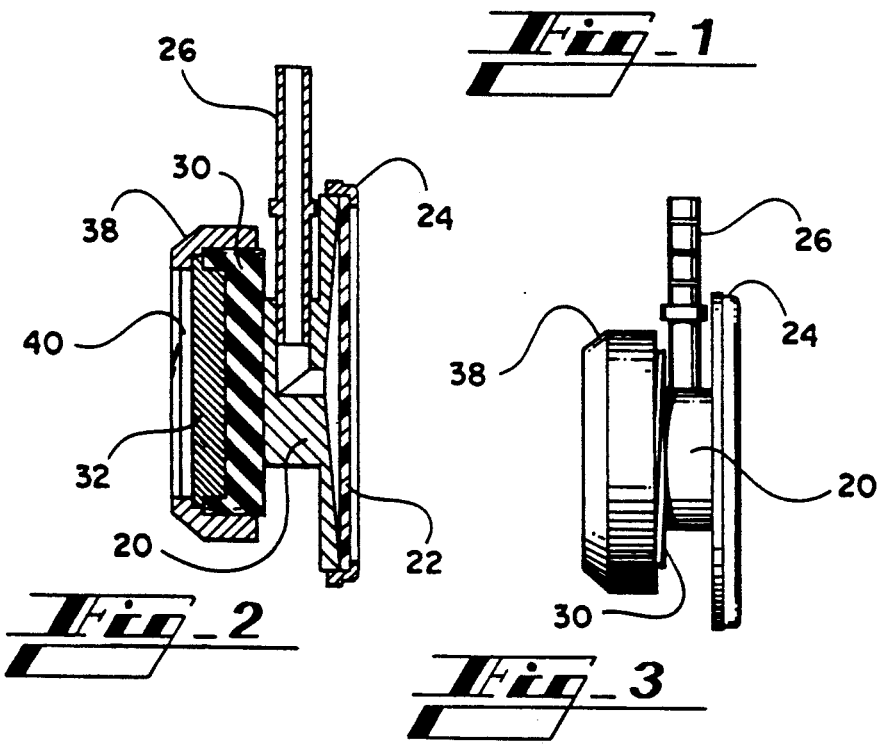
Fig_2
Fig_3
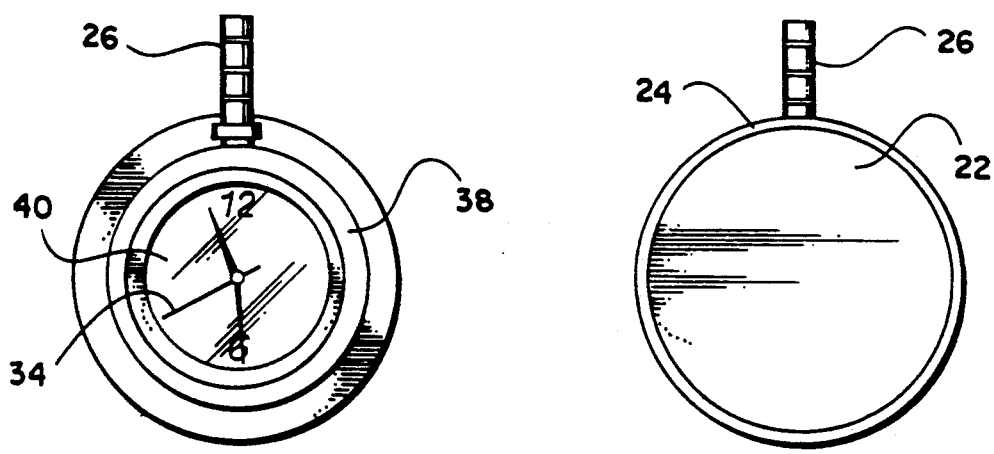
Fig_4
Fig_5

STETHOSCOPE

TECHNICAL FIELD OF THE INVENTION

The invention relates to stethoscopes, and more particularly to a combined stethoscope and watch.

BACKGROUND OF THE INVENTION

When medical personnel use a stethoscope it is often necessary that sounds heard through the stethoscope be listened to over a selected period of time. For example, in observing the rate of a patient's heart beat it is necessary to monitor the sound of the heart beat for a period sufficient to calculate the number of heart beats per minute. Since it is necessary to place the stethoscope at a precise location on the patient's body and accurately monitor elapsing time simultaneously, it would be desirable to have a stethoscope head and watch that can be viewed simultaneously. A convenient method of accomplishing this objective is to have a watch that is combined with a stethoscope head. A combined stethoscope head and digital watch are disclosed in U.S. Pat. No. 285,964 issued to Ziebol. However, in the health care profession it is desirable, and in some instances required, that a watch with a sweeping second hand be used to monitor elapsing time. Combining a sweeping-second-hand watch with a stethoscope may cause a problem in that the sweeping second hand is driven by a motor and the motor creates sounds which may interfere with the use of the stethoscope.

SUMMARY OF THE INVENTION

It is an object of the invention to provide a combined stethoscope head and watch with a sweeping second hand.

It is also an object of the invention to provide such a combined stethoscope and watch wherein the sound from the watch does not interfere with the use of the stethoscope.

It is a further object of the invention to provide a combined stethoscope and watch with sweeping second hand that is easily serviceable.

The present invention is directed to a combined stethoscope and watch with a sweeping second hand. The invention is constructed so that any sounds emanating from the watch do not interfere with the use of the stethoscope. The watch is also easily serviceable. For example, a battery which powers the watch may be easily changed.

Other aspects, objects, features, and advantages of the present invention will become apparent to those skilled in the art upon reading the detailed description of preferred embodiments in conjunction with the accompanying drawings and appended claims.

BRIEF DESCRIPTION OF THE DRAWINGS

FIG. 1 is an isometric illustration of a combined stethoscope head and watch with a sweeping second hand embodying teachings of the invention.

FIG. 2 is a sectional view of the invention of FIG. 1.
FIG. 3 is a side view of the invention of FIG. 1.
FIG. 4 is a top view of the invention of FIG. 1.
FIG. 5 is a rear view of the invention of FIG. 1

DETAILED DESCRIPTION OF A PREFERRED EMBODIMENT OF THE INVENTION

While the specification concludes with claims particularly pointing out and distinctly claiming the subject matter which is regarded as the present invention, the invention will now be described with reference to the following description of an embodiment taken in conjunction with the accompanying drawings.

Reference will be made to FIGS. 1 through 5 in which the same numbers are indicative of the same elements throughout the figures. A stethoscope head 10 embodying the teachings of the present invention is illustrated in FIG. 1. The description which follows encompasses features illustrated in all of the figures, however, attention is particularly directed to the sectional view of FIG. 2 which illustrates all of the features of the invention. A stethoscope housing 20 provides the foundation for the invention 10. Sounds are transmitted to the invention 10 through a membrane 22. The membrane is normally placed on the person being examined. The membrane 22 may be affixed to the stethoscope housing 20 via a membrane cover 24. A listening tube attachment 26 extends from the stethoscope housing 20. Health care personnel hear the sounds transmitted from the stethoscope head through ear tubes. Either a single or double ear tube is attached to the stethoscope housing 20 via the listening tube attachment 26. A watch support member 30 extends from the stethoscope housing 20. The watch support member 30 illustrated is threaded. The watch support member 30 serves two functions: (1) Provides a support base for the watch 32. (2) Insulates the stethoscope housing 20 from the sounds of the watch 32. The watch 32 rests upon the watch support member 30. The watch housing 38 fits over the watch 32 and is secured to the watch support member 30. The watch housing 38 may be secured to the watch support member 30 by several means. The means illustrated is by providing a threaded watch support member 30 and a watch housing 38 that has cooperating, reciprocal threads. The two pieces may also be joined by providing a snap-fit structure wherein there is a cooperating lip and receiving ring. Providing a removable watch housing 38 ensures access to the watch 32 so that it may be easily serviced, such as for changing a battery or replacing the watch 32 itself. The watch housing 38 also engages the edge of the watch 32 to secure it. This prevents the watch from moving about, being unnecessarily jarred and rotating to a position where it can not be easily read. When the screw-on watch housing 38 is used the watch 32 may be placed into a desired reading position and then secured in that position by tightening the watch housing 38 with respect to the watch support member 30. The watch 32 is engaged by the watch housing 38 in such a manner that the face of the watch 32 is not obstructed, thus allowing the sweeping second hand 34 to rotate. The face of the watch 32 is protected by a crystal 40.

It is important that any sounds emanating from the watch 32 are not transmitted to the stethoscope housing 20. There are several ways that this objective may be achieved. One way is to use a watch that produces no sound. This may be difficult because a sweeping second hand 34 must be driven by a motor and motors produce sound. Another method is to insulate the sounds of the watch 32 from the stethoscope housing 20. This can be accomplished in several ways. The watch support member 30 may be constructed of sound-insulating type material such as rubber or plastic. Hard rubber or plastic provides sound insulation while still being firm and durable enough to allow for mating between the watch support member 30 and the watch housing 38. Another method of insulating watch 32 sounds is to interposed a piece of sound-insulating material 36 between the watch support member 30 and the stethoscope housing 20.

With the invention 10, a health care worker may place the membrane 22 upon the desired portion of a patient's body and monitor sounds through the stethoscope 10 while observing the requisite time period from the sweeping second hand 34. The worker's attention is simultaneously directed to the location of the stethoscope 10 and the face of the watch 32. The user is able to ensure that the device 10 is at the proper location during observation and monitoring. Also, the user may easily make minor adjustments in the location of the device while still monitoring body sounds and elapsing time. In addition, major changes in the positioning of the stethoscope 10 may be achieved and monitoring resumed very quickly.

As should be apparent from the foregoing specification, the invention is susceptible of being modified with various alterations and modifications which may differ from those which have been described in the preceding specification and description. Accordingly, the following claims are intended to cover all alterations and modifications which do not depart from the spirit and scope of the invention.

What is claimed is:

1. A stethoscope head comprising:
 a pickup head;
 means for attaching a sound conveyance tube to said pickup head;
 a watch having a face with a sweeping second hand;
 means for attaching said watch having a face with a sweeping second hand to said pickup head; and
 sound-insulation means interposed between said watch having a face with a sweeping second hand and said pickup head.

2. A stethoscope head comprising:
 a pickup head;
 means for attaching a sound conveyance tube to said pickup head;
 a watch having a face with a sweeping second hand;
 a watch support member attaching said watch having a face with a sweeping second hand to said pickup head; and
 sound-insulation means interposed between said watch support member and said pickup head.

3. A stethoscope comprising:
 a pickup head;
 means for attaching sound conveyance tube to said pickup head;
 a watch support member extending from said pickup head;
 a watch having a face with a sweeping second hand;
 a watch crystal covering said face of said watch;
 a watch housing for encasing said watch, defining an opening through which said face of said watch is visible;
 means for securing said watch housing to said watch support member; and
 sound-absorbing material interposed between said pickup head and said watch support member.

4. The invention of claim 3, said sound-absorbing material comprising plastic.

* * * * *